US012605065B2

(12) United States Patent
Gawish et al.

(10) Patent No.: US 12,605,065 B2
(45) Date of Patent: Apr. 21, 2026

(54) METHOD AND SYSTEM FOR AUTOMATIC PUPIL DETECTION

(71) Applicant: GOOGLE LLC, Mountain View, CA (US)

(72) Inventors: Ahmed Gawish, Waterloo (CA); Idris S. Aleem, Kitchener (CA)

(73) Assignee: GOOGLE LLC, Mountain View, CA (US)

( * ) Notice: Subject to any disclaimer, the term of this patent is extended or adjusted under 35 U.S.C. 154(b) by 899 days.

(21) Appl. No.: 17/434,127

(22) PCT Filed: Jul. 27, 2020

(86) PCT No.: PCT/CA2020/051029
§ 371 (c)(1),
(2) Date: Aug. 26, 2021

(87) PCT Pub. No.: WO2021/016704
PCT Pub. Date: Feb. 4, 2021

(65) Prior Publication Data
US 2022/0142473 A1     May 12, 2022

Related U.S. Application Data

(60) Provisional application No. 62/878,840, filed on Jul. 26, 2019.

(51) Int. Cl.
*A61B 3/11* (2006.01)
*A61B 3/00* (2006.01)

(52) U.S. Cl.
CPC ............ *A61B 3/111* (2013.01); *A61B 3/0041* (2013.01)

(58) Field of Classification Search
CPC .......... A61B 3/0041; A61B 3/11; A61B 3/111
See application file for complete search history.

(56) References Cited

U.S. PATENT DOCUMENTS 9,911,395 B1      3/2018   Townsend et al.
2004/0189935 A1   9/2004   Warden et al.
(Continued)

FOREIGN PATENT DOCUMENTS

JP        H08238222 A       9/1996
JP        2008029702 A      2/2008
(Continued)

OTHER PUBLICATIONS

International Search Report and Written Opinion mailed Oct. 28, 2020 for corresponding International Application No. PCT/CA2020/051029, 12 pages.
(Continued)

*Primary Examiner* — Jack Dinh

(57) ABSTRACT

Systems and methods of detecting pupillary positions on a head of a subject are described. While a camera and a light source are positioned in front of the head of the subject, the camera is caused to capture image data representative of a frontal portion of the head of the subject. From the image data, a face of the subject is detected. Up to two eyes are identified from the detected face. A reflection of the light source on each identified eye is detected. A pupillary position of each identified eye is estimated based on a position of the detected light source reflection on the identified eye. One or more of interpupillary distance, left pupil distance, and right pupil distance may be determined from the estimated pupillary positions.

19 Claims, 12 Drawing Sheets

(56) References Cited

U.S. PATENT DOCUMENTS

| | | | |
|---|---|---|---|
| 2011/0085139 | A1 | 4/2011 | Blixt et al. |
| 2013/0002846 | A1 | 1/2013 | De Bruijn et al. |
| 2013/0314668 | A1 | 11/2013 | Haddadi et al. |
| 2016/0085301 | A1 | 3/2016 | Lopez |
| 2016/0379093 | A1 | 12/2016 | Yoshioka et al. |
| 2017/0047046 | A1 | 2/2017 | Tam |
| 2018/0275410 | A1 | 9/2018 | Yeoh et al. |

FOREIGN PATENT DOCUMENTS

| | | | |
|---|---|---|---|
| KR | 20160092669 | A | 8/2016 |
| KR | 1020160092669 | A | 8/2016 |
| WO | 2015148149 | A1 | 10/2015 |
| WO | 2019034231 | A1 | 2/2019 |

OTHER PUBLICATIONS

Extended European Search Report mailed Sep. 29, 2022 for European Application No. 20848452.7, 36 pages.

Michael Xuelin Huang, Csxhuang@Comp Polyu Edu HK et al: "ScreenGlint: Practical, In-situ Gaze Estimation on Smartphones", Interaction Design and Children, ACM, May 2, 2017, pp. 2546-2557.

Nadeem Iqbal et al.: "A Study on Human Gaze Estimation Using Screen Reflection", SAT 2015 18th International Conference, Sep. 24-27, 2015; Nov. 2, 2008, pp. 104-111.

International Preliminary Report on Patentability mailed Feb. 10, 2022 for corresponding International Application No. PCT/CA2020/051029, 10 pages.

Translation of Notification of First Office Action mailed Oct. 31, 2023 for CN Application No. 202080021767.6, 21 pages.

Communication Pursuant to Article 94(3) EPC mailed Nov. 27, 2024 for EP Application No. 20848452.7, 8 pages.

Kim, Sangwook et al., "Gaze Tracking Based on Pupil Estimation Using Multilayer Perception", Proceedings of International Joint Conference on Neural Networks, San Jose, California, Jul. 31-Aug. 5, 2011, 7 pages.

Translation of Chinese Office Action mailed Apr. 19, 2024 for CN Application No. 202080021767.6, 20 pages.

Translation of Chinese Notice of Allowance mailed Jul. 12, 2024 for CN Application No. 202080021767.6, 6 pages.

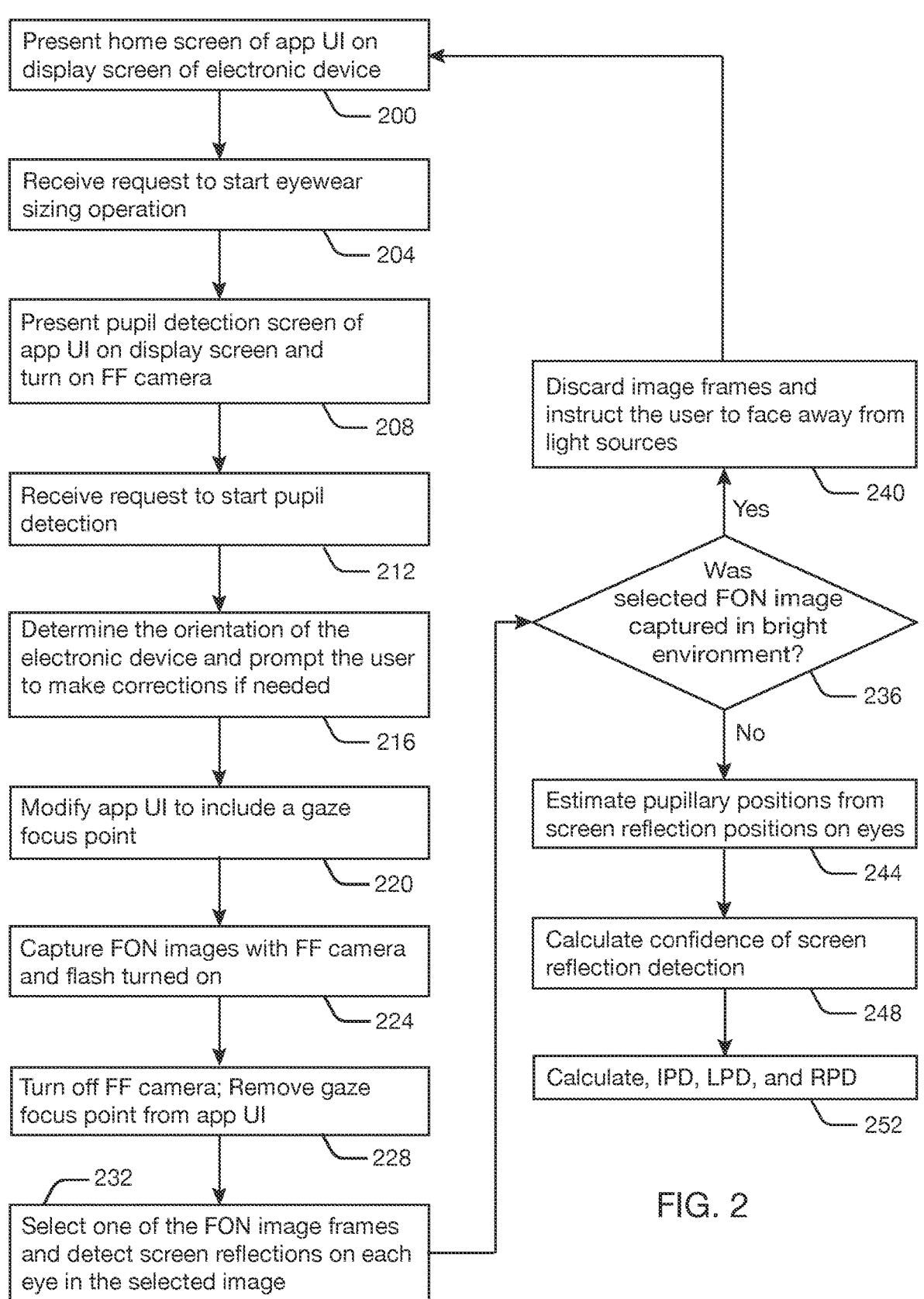

Present home screen of app UI on display screen of electronic device
— 200

Receive request to start eyewear sizing operation
— 204

Present pupil detection screen of app UI on display screen and turn on FF camera
— 208

Receive request to start pupil detection
— 212

Determine the orientation of the electronic device and prompt the user to make corrections if needed
— 216

Modify app UI to include a gaze focus point
— 220

Capture FON images with FF camera and flash turned on
— 224

Turn off FF camera; Remove gaze focus point from app UI
— 228

— 232
Select one of the FON image frames and detect screen reflections on each eye in the selected image Discard image frames and instruct the user to face away from light sources
— 240

Yes

Was selected FON image captured in bright environment?
— 236

No

Estimate pupillary positions from screen reflection positions on eyes
— 244

Calculate confidence of screen reflection detection
— 248

Calculate, IPD, LPD, and RPD
— 252

Focus on the timer at the top.

1

METHOD AND SYSTEM FOR AUTOMATIC PUPIL DETECTION

CROSS-REFERENCE TO RELATED APPLICATIONS

The present application is a U.S. National Stage under 35 U.S.C. § 371 of International Patent Application Serial No. PCT/CA2020/051029, entitled "Method and System for Automatic Pupil Detection" and filed on Jul. 27, 2020, which claims priority to U.S. Provisional Application No. 62/878,840, filed on Jul. 26, 2019, the entireties of which are incorporated by reference herein.

BACKGROUND

There has been considerable interest in turning eyeglasses into wearable electronic devices. Various permutations of these wearable electronic devices have included eyeglasses with integrated cameras (e.g., SPECTACLES by Snap Inc.), eyeglasses with integrated audio (e.g., BOSE FRAMES ALTO audio sunglasses), and eyeglasses with integrated displays (e.g., FOCALS by North Inc. and VUZIX BLADE®). These wearable electronic devices are often generically referred to as smart glasses. However, the complexities of these devices can vary widely depending on the features supported by the devices. Smart glasses that provide displays may be referred to as wearable heads-up displays (WHUDs) to distinguish them from smart glasses that do not provide displays.

One class of WHUDs is virtual retinal display, where a projector draws a raster scan onto the eye of the user, i.e., the person wearing the WHUD. The WHUD includes a support frame that has the appearance of eyeglasses frames. The support frame holds two lenses. The projector is mounted in a temple of the support frame, and an optical combiner that is integrated in one of the lenses receives light from the projector and redirects the light to the eye. The optical combiner may be a free-space combiner, e.g., a holographic combiner, or a substrate-guided combiner, e.g., a waveguide or lightguide combiner with input and output couplers. The WHUD has an eyebox that defines a range of eye positions over which display content is visible to the user. The eyebox may be defined by a single exit pupil or multiple exit pupils, depending on the configuration of the optical combiner that forms the exit pupil(s). Typically, when the eye of the user is positioned inside the eyebox, or when the pupil of the eye is aligned with at least one exit pupil, the user will be able to see all of the display content. In contrast, when the eye of the user is positioned outside of the eyebox, the user will not be able to see at least some of the display content.

Like normal eyeglasses, the WHUD includes a support frame (or frames) that needs to be sized and fitted to the head and lenses that need to be fitted to the support frame, where the lenses may or may not carry prescriptions. Unlike normal eyeglasses, the WHUD has an extra requirement related to alignment of the eye with the eyebox and placement of an optical combiner on a lens. The optical combiner has to be placed on the lens and relative to the support frame in a manner that ensures that the user will be able to see display content when the support frame is mounted on the head of the user, and this placement has to be customized for each user. One of the key measurements made to size a WHUD, or any eyewear in general, is interpupillary distance (IPD) (also known as pupillary distance (PD)). IPD is the distance, typically measured in millimeters, between the centers of the pupils. Other measurements related to IPD are left pupillary distance (LPD) and right pupillary distance (RPD). LPD is the distance from the left pupil center to the center of the nose bridge, and right pupil distance (RPD) is the distance from the right pupil center to the center of the nose bridge. If the eyes are perfectly symmetric about the center of the nose bridge and are looking straight ahead or at infinity, LPD should be equal to RPD, which should be equal to half of IPD. In normal eyeglasses with prescription and WHUDs with prescription, IPD is used to determine where the optical centers of the lenses should be. In addition, in WHUDs, IPD (or IPD together with LPD or RPD), is used to determine the optimum placement of the optical combiner on the lens.

Eye doctors (e.g., optometrists or ophthalmologists) may provide pupillary position measurements such as IPD as part of eye exams and prescription information. However, requiring that a potential user should visit an eye doctor for an eye exam before being sized for a WHUD would present a high barrier to wide scale adoption of the WHUD. There are manual methods of measuring IPD. One manual method is based on physically measuring the distance between the pupils using a ruler that is placed against the forehead. However, such manual methods may not yield sufficiently precise pupillary position measurements for sizing of a WHUD that is intended to project content into the eye through an eyebox.

SUMMARY OF EMBODIMENTS

A computer-implemented method of detecting pupillary positions on a head of a subject may be summarized as including: while a camera and a light source are positioned in front of the head of the subject, causing the camera to capture image data representative of a front portion of the head of the subject; detecting a face of the subject from the image data; identifying up to two eyes from the detected face; detecting a reflection of the light source on each identified eye; and estimating a pupillary position of each identified eye based on a position of the detected light source reflection on the identified eye.

In some cases, the method includes causing the light source to illuminate the frontal portion of the head of the subject contemporaneously with causing the camera to capture the image data.

In some cases, the light source is a display screen of an electronic device, and detecting the reflection of the light source on each identified eye includes detecting a reflection of the display screen on each identified eye.

In some cases, detecting the reflection of the display screen on each identified eye includes convolving a region of the detected face including the identified eye with a convolution kernel that is constructed to identify a bright area that has a screen reflection shape and that is surrounded by relatively darker pixels.

In other cases, detecting the reflection of the display screen on each identified eye includes convolving a region of the detected face including the identified eye with a first convolution kernel and a second convolution kernel. The first convolution kernel is constructed to identify a bright area having a screen reflection shape and that is surrounded by relatively darker pixels. The second convolution kernel is constructed to identify dark pixels that surround a relatively brighter area having a screen reflection shape.

In some cases, the method includes presenting a gaze focus point on the display screen prior to causing the camera to capture the image data.

In some cases, the method includes directing a gaze of the subject to the gaze focus point prior to causing the camera to capture the image data.

In some cases, estimating the pupillary position of each identified eye includes determining a point on the respective detected screen reflection corresponding to the gaze focus point on the display screen.

In some cases, estimating the pupillary position of each identified eye includes applying a lateral shift to the determined point on the respective detected screen reflection to compensate for an offset between an optical axis and a visual axis of the identified eye.

In some cases, the method includes determining whether a lighting condition of the frontal portion of the head of the subject indicates a bright environment during at least a portion of causing the camera to capture the image data.

In some cases, determining whether the lighting condition of the frontal portion of the head of the subject indicates a bright environment includes determining for at least one identified eye whether there are extra light source reflections on the at least one identified eye and comparing the average intensity of each of the extra light source reflections to an average intensity of the detected light source reflection on the at least one identified eye. The lighting condition of the frontal portion of the head of the subject indicates a bright environment if there is at least one extra light source reflection on the at least one identified eye with an average intensity that substantially matches the average intensity of the detected light source reflection on the at least one identified eye.

In some cases, if it is determined that the lighting condition of the frontal portion of the head of the user indicates a bright environment, the method includes redoing causing the camera to capture image data representative of the frontal portion of the head of the subject with a different lighting condition.

In some cases, the method includes prompting the subject to face away from extra light sources to provide the different lighting condition.

In some cases, the method includes determining a confidence of the estimate of the pupillary position of each identified eye based on a degree of displacement of the pupillary position of the identified eye from a center position of an iris on the identified eye.

In some cases, the method includes determining at least one of an interpupillary distance, a left pupillary distance, and a right pupillary distance from the estimated pupillary positions.

A system for detecting pupillary positions on a head of a subject may be summarized as including: a front facing camera; a display screen; at least one processor communicatively coupled to the front facing camera and the display screen; and memory storing a set of instructions that as a result of execution by the at least one processor cause the system to: capture image data representative of a frontal portion of the head of the subject using the front facing camera; detect a face of the subject in the image data; identify up to two eyes from the detected face; detect a reflection of the display screen on each identified eye; and estimate a pupillary position of each identified eye based on a position of the detected screen reflection on the identified eye.

A non-transitory computer-readable storage medium has computer executable instructions stored thereon that as a result of being executed cause at least one computer processor to: obtain image data representative of a frontal portion of a head of a subject; detect a face of the subject from the image data; identify up to two eyes from the detected face; detect a reflection of a light source having a known shape on each identified eye; and estimate a pupillary position of each identified eye based on a position of the detected light source reflection on the identified eye.

The foregoing general description and the following detailed description are exemplary of the invention and are intended to provide an overview or framework for understanding the nature of the invention as it is claimed. The accompanying drawings are included to provide further understanding of the invention and are incorporated in and constitute part of this specification. The drawings illustrate various embodiments of the invention and together with the description serve to explain the principles and operation of the invention.

BRIEF DESCRIPTION OF DRAWINGS

In the drawings, identical reference numbers identify similar elements or acts. The sizes and relative positions of elements in the drawings are not necessarily drawn to scale.

For example, the shapes of various elements and angles are not necessarily drawn to scale, and some of these elements are arbitrarily enlarged and positioned to improve drawing legibility. Further, the particular shapes of the elements as drawn are not necessarily intended to convey any information regarding the actual shape of the particular elements and have been solely selected for ease of recognition in the drawing.

FIG. 2 is a flowchart illustrating a method of automatically detecting pupillary positions on a head.

DETAILED DESCRIPTION

Figure 1:
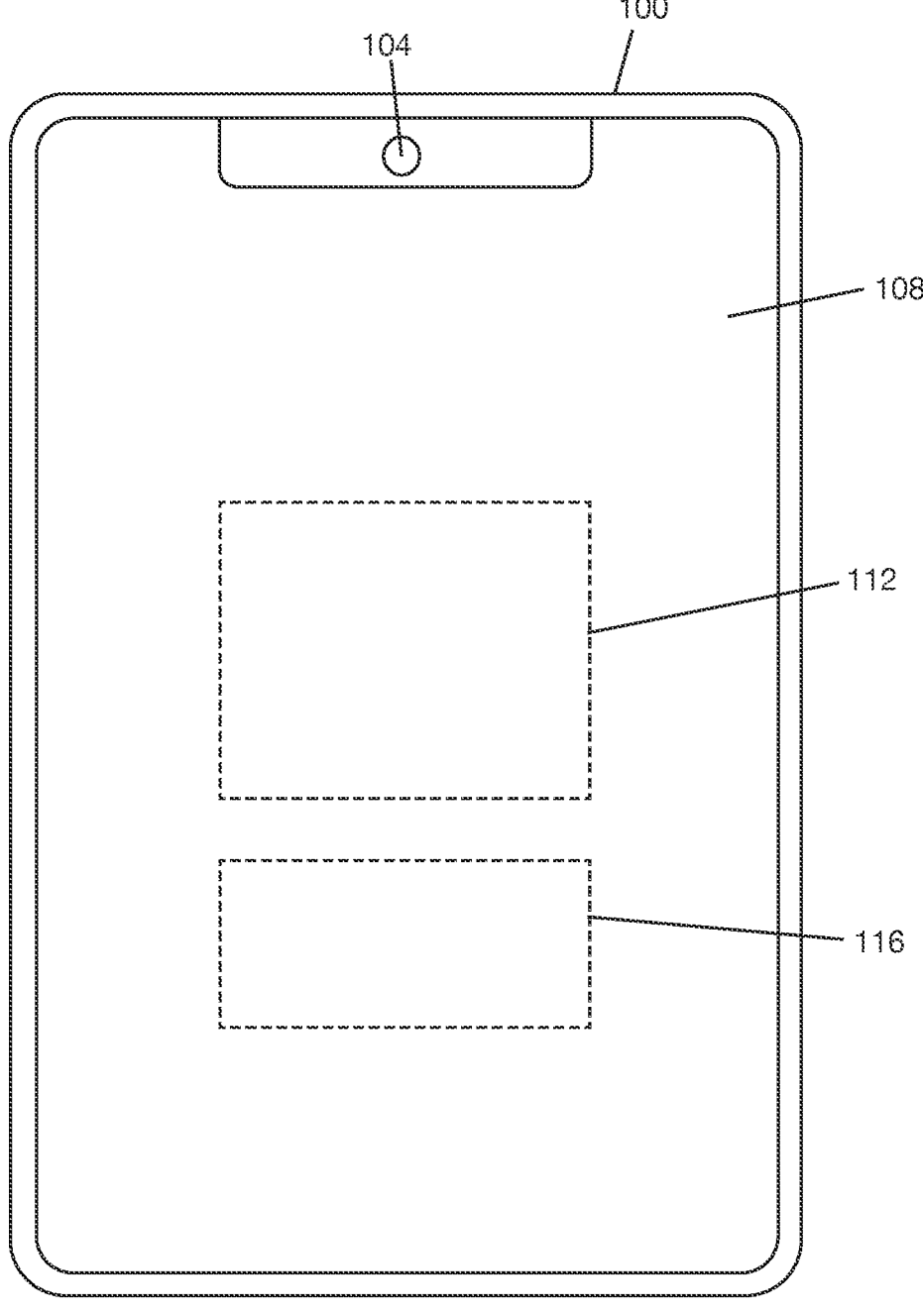
FIG. 1 is a front view of an exemplary electronic device that may be configured to automatically detect pupillary positions on a head of a user.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with portable electronic devices and head-worn devices have not been shown or described in detail to avoid unnecessarily obscuring descriptions of the embodiments. For the sake of continuity, and in the interest of conciseness, same or similar reference characters may be used for same or similar objects in multiple figures. For the sake of brevity, the term "corresponding to" may be used to describe correspondence between features of different figures. When a feature in a first figure is described as corresponding to a feature in a second figure, the feature in the first figure is deemed to have the characteristics of the feature in the second figure, and vice versa, unless stated otherwise.

In this disclosure, unless the context requires otherwise, throughout the specification and claims which follow, the word "comprise" and variations thereof, such as, "comprises" and "comprising" are to be construed in an open, inclusive sense, that is as "including, but not limited to."

In this disclosure, reference to "one implementation" or "an implementation" or to "one embodiment" or "an embodiment" means that a particular feature, structures, or characteristics may be combined in any suitable manner in one or more implementations or one or more embodiments.

In this disclosure, the singular forms "a," "an," and "the" include plural referents unless the content clearly dictates otherwise. It should also be noted that the term "or" is generally employed in its broadest sense, that is, as meaning "and/or" unless the content clearly dictates otherwise.

The headings and Abstract of the disclosure provided herein are for convenience only and do not interpret the scope or meaning of the embodiments.

FIG. 1 illustrates a portable electronic device (PED) 100 that may be configured to automatically detect pupillary positions on a head of a subject according to a method described herein. The term "pupillary position" refers to a center position of a pupil of an eye. For a typical user with two eyes, there will be two pupillary positions, from which IPD can be calculated, or if a gaze point is known, exact LPD and RPD can be determined. Although electronic device 100 is described as portable, it should be recognized that the method may be implemented in an electronic device that may not be considered to be portable. For illustration purposes, PED 100 is depicted as a smartphone in FIG. 1, but the method of detecting pupillary positions may be practiced with other types of portable electronic devices, such as tablets or notebook computers. Also, the smartphone illustrated in FIG. 1 as PED 100 is simplistic and does not indicate all the features that a smartphone may have. In general, a PED (or electronic device in general) that may be configured to detect pupillary positions is a system that includes a camera and a light source, where the positions and geometry of the camera and light source during use of the system are fixed and known. In one example, PED 100 includes, among other electronic components, a front facing (FF) camera 104 (or "selfie" camera), a display screen 108, which functions as a light source, at least one processor to execute computer-readable instructions 112, and memory 116 to store data and computer-readable instructions. The term "front facing camera" or "FF camera" mainly indicates that the camera is facing the user while the user is operating PED 100. Memory 116 includes one or more types of data storage, such as random-access memory (RAM), read-only memory (ROM), Flash memory, solid state drive, and the like. PED 100 may have an electronic front-facing (FF) flash that can be selectively activated (or turned on) when capturing images with FF camera 104. On smartphones, FF flash is typically activated by displaying a white screen with maximum brightness on the display screen.

In one implementation, to allow PED 100 to be used for detecting pupillary positions on a head of a subject user, an eyewear sizing app is stored in memory 116 of electronic device 100. For example, upon request from the subject user, processor 112 may obtain the eyewear sizing app from an app store and store the app in memory 116. The user may activate the eyewear sizing app using any suitable method for starting an app on the electronic device (e.g., by selecting an icon in a menu presented on display screen 108 or by voice command). In implementations herein, the eyewear sizing app generally includes computer-readable instructions to capture an image of a scene in front of FF camera 104 and extract pupillary position information from the captured image. FF camera 104 is positioned in front of the head of the subject user so that the scene captured by the FF camera includes a frontal portion of the head. The frontal portion of the head is the portion of the head including the face. Any suitable method of positioning the FF camera 104 in front of the head of the user may be used, such as the user holding PED 100 in a selfie position or by supporting PED 100 on a tripod or selfie stick or the like that is positioned in front of the user.

FF cameras, such as those provided with smartphones, typically do not capture high resolution images. Thus, pupil data are very difficult, and sometimes impossible, to extract directly from FF camera images. Herein, an approach that does not depend on extracting pupil data from FF camera images is used to detect pupillary positions. It has been discovered that if an FF camera captures an image of a frontal portion of the head with the flash turned on, there will be a reflection of the display screen in each of the pupils of the eye. These screen reflections can be detected and used as an accurate estimate of the pupil centers, particularly if the gaze direction of the subject user is known. To ensure that the screen reflections can be detected accurately, the approach includes an assessment of the lighting conditions in which the FF camera image was captured. In the event that the lighting conditions might lead to ambiguities in detecting the screen reflections, the user is prompted to make changes in the environment of the FF camera so that a better FF camera image may be captured.

Figure 3A:
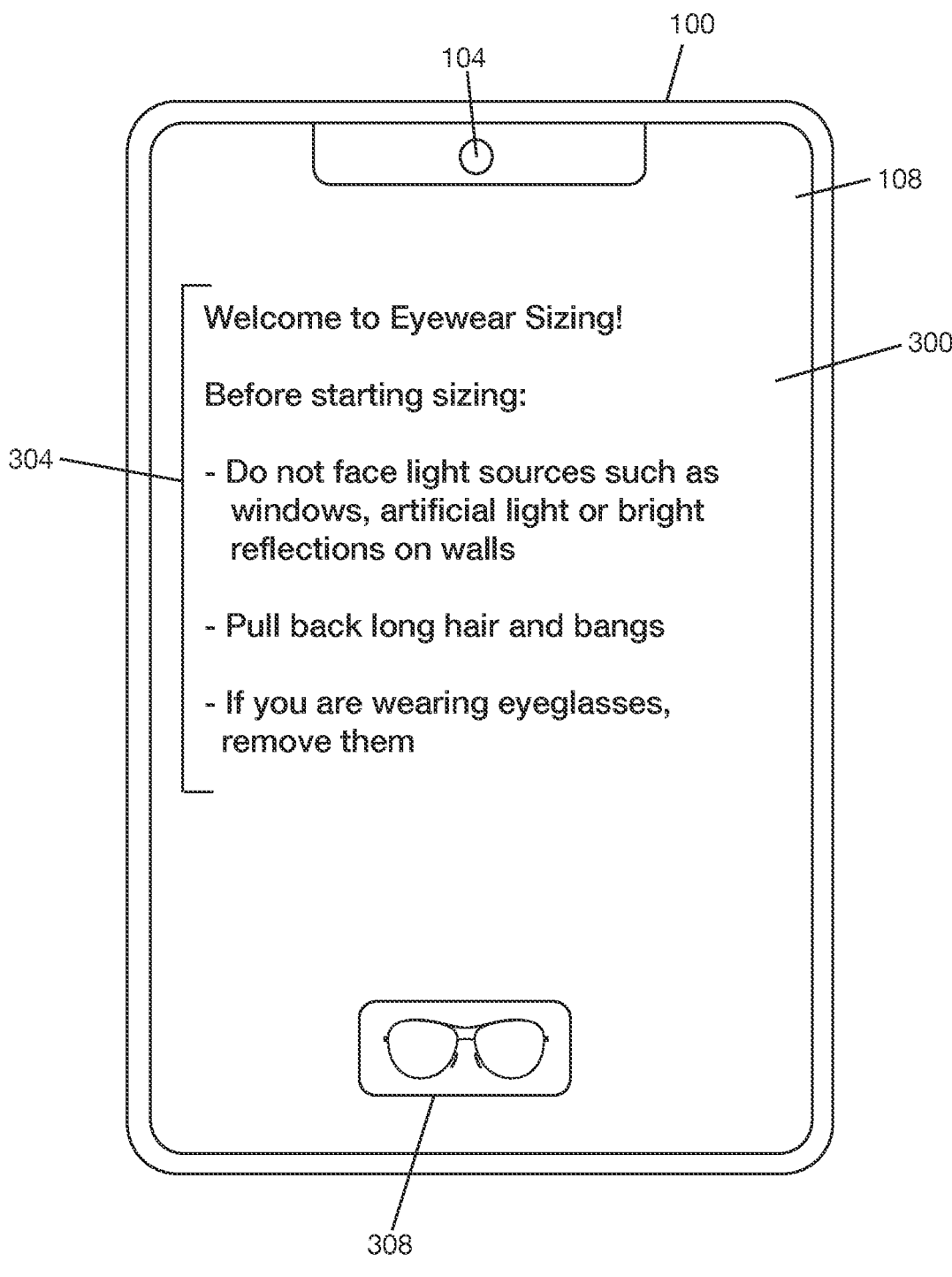
FIG. 3A is a front view of the electronic device of FIG. 1 showing an exemplary home screen of a UI of an eyewear sizing app (app UI).

FIG. 2 is a flow chart illustrating a method of detecting pupillary positions on a head of a subject user. The method illustrated in FIG. 2 and described below can be provided as a set of instructions (or eyewear sizing app) stored in a memory of an electronic device (e.g., PED 100 in FIG. 1) and executable by at least one processor of the electronic device. At 200, a processor of an electronic device (e.g., processor 112 in FIG. 1) causes a user interface (UI) of the eyewear sizing app (hereafter referred to as app UI) to be presented on a display screen of the electronic device (e.g., display screen 108 in FIG. 1). The app UI may be presented in response to a user accessing the eyewear sizing app on the electronic device, e.g., by selecting an icon that represents the eyewear sizing app or by a verbal command. FIG. 3A shows an example home screen of app UI 300 on display screen 108 of PED 100. The details of the home screen are design elements and could be different from what is shown in FIG. 3A. For illustrative purposes, the home screen of app UI 300 may include a set of instructions or information 304 related to use of the eyewear sizing app and a button 308. In one implementation, button 308 is set up with an action to start the eyewear sizing operation (or WHUD sizing operation). After reading the instructions 304, the user may select button 308 to start the eyewear sizing operation.

Figure 3B:
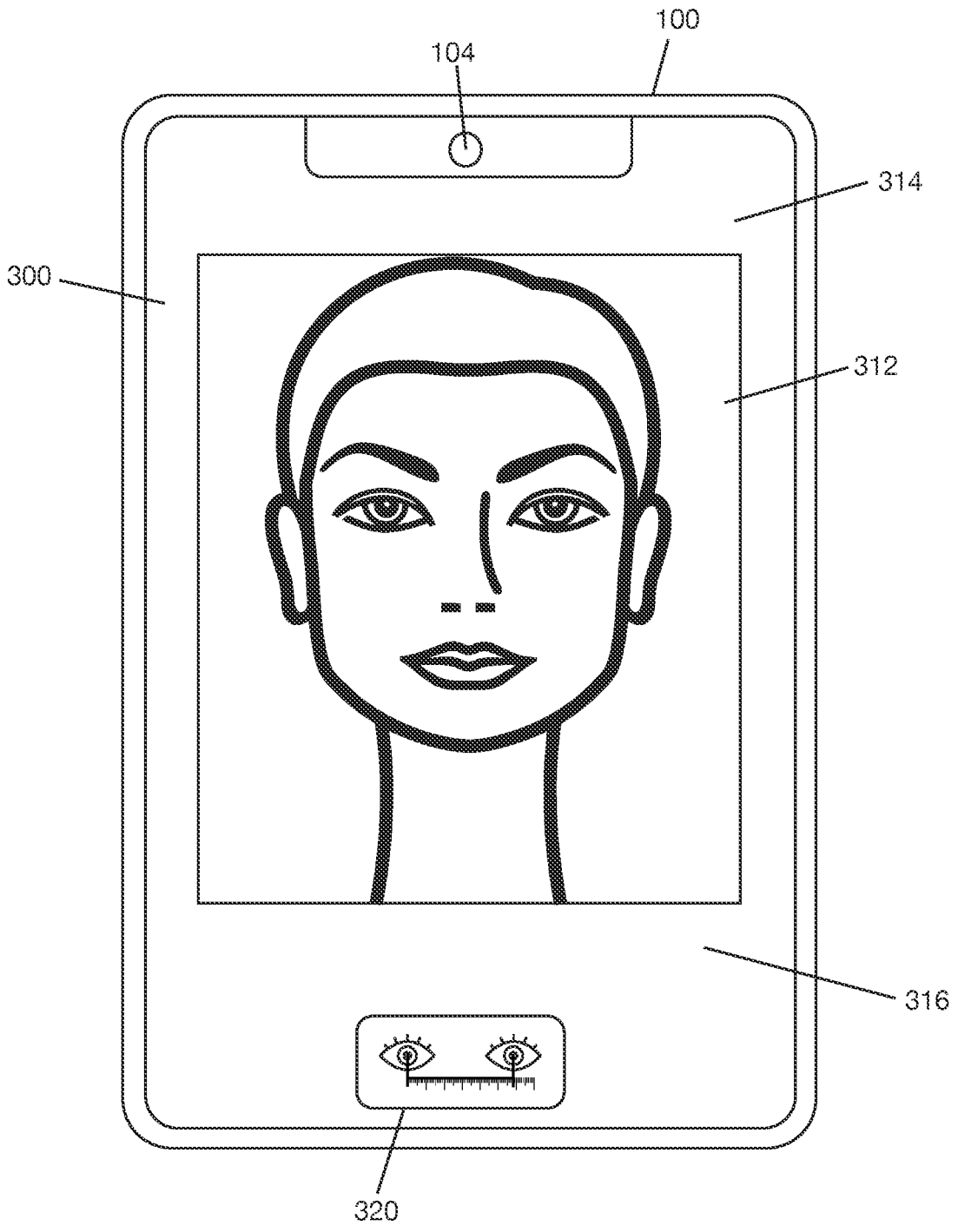
FIG. 3B is a front view of the electronic device of FIG. 1 showing an exemplary pupil detection screen of an app UI.

Returning to FIG. 2, at 204, the processor receives a request to start the eyewear sizing operation. In response to the request to start the eyewear sizing operation, at 208, the processor presents a pupil detection screen of the app UI on the display screen. The processor may further turn on the FF camera (e.g., camera 104 in FIG. 1). For illustrative purposes, FIG. 3B shows an example pupil detection screen of app UI 300 on display screen 108. The details of the pupil detection screen are design elements and could be different from what is shown in FIG. 3B. For illustration purposes, the pupil detection screen includes a capture window 312, a top bar 314 above capture window 312, and a bottom bar 316 below capture window 312. Since the processor has turned FF camera 104 on, a scene in front of FF camera 104 (in this case, the user operating PED 100) is shown within capture window 312. Bottom bar 316 includes a button 320. In one implementation, button 320 is set up with an action to start the pupil detection process. The user may select button 320 to start the pupil detection process. While the pupil detection process is running, feedback about the process may be displayed in the bottom bar 316 and/or top bar 314.

Figure 3C:
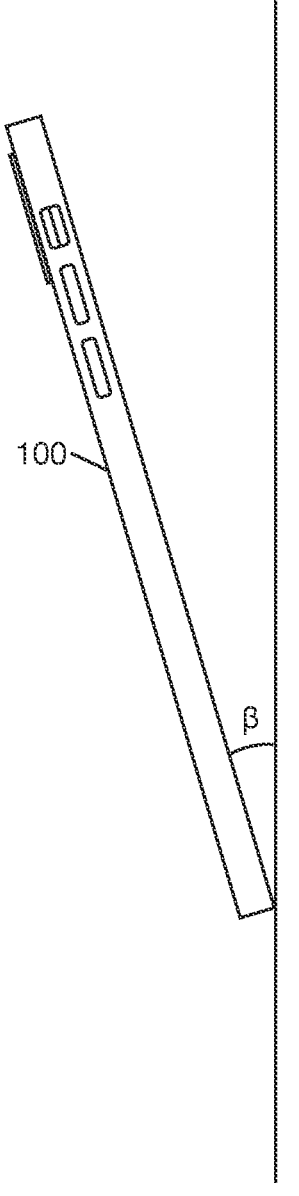
FIG. 3C is a side view of an electronic device tilted relative to the vertical.

Returning to FIG. 2, at 212, the processor receives a request to start the pupil detection process. In response to receiving the request to start the pupil detection process, the processor may perform some preliminary checks. For example, the upper eyelid normally occludes a portion of the eye. In general, the lower the gaze of the eye, the greater the portion of the eye that will be occluded by the upper eyelid. Thus, it is preferable that the eye is not looking down to such a degree that the upper eyelid substantially covers the pupil when an image of the face of the user is captured for pupil detection purposes. FIG. 3C shows an example of PED 100 (and therefore the camera 104 included in PED 100) in a tilted position relative to the vertical (direction of gravity). The angle between PED 100 and the vertical is represented by β and may be referred to hereafter as tilt angle. A tilt angle threshold outside of which it is likely that the gaze of the eye is too low can be determined a priori. As a non-limiting example, a tilt angle threshold may be 20 degrees. Returning to FIG. 2, in one implementation, at 216, the processor determines a tilt angle of the electronic device (e.g., PED 100) relative to the vertical. The processor may obtain the measurements needed to determine the tilt angle of the electronic device from a sensor unit in the electronic device, such as an inertial motion unit (IMU). The processor determines if the tilt angle of the electronic device (i.e., the angle between the electronic device and the vertical) exceeds the tilt angle threshold. If the tilt angle exceeds the tilt angle threshold, the processor may prompt the user to hold the device higher up (e.g., by displaying a suitable message on the app UI), which will force the tilt angle to reduce. The processor may repeat determining the tilt angle of the electronic device relative to the vertical and checking if the tilt angle is outside of an acceptable range until the user has made the proper adjustment to the orientation of the device.

Figure 3D:
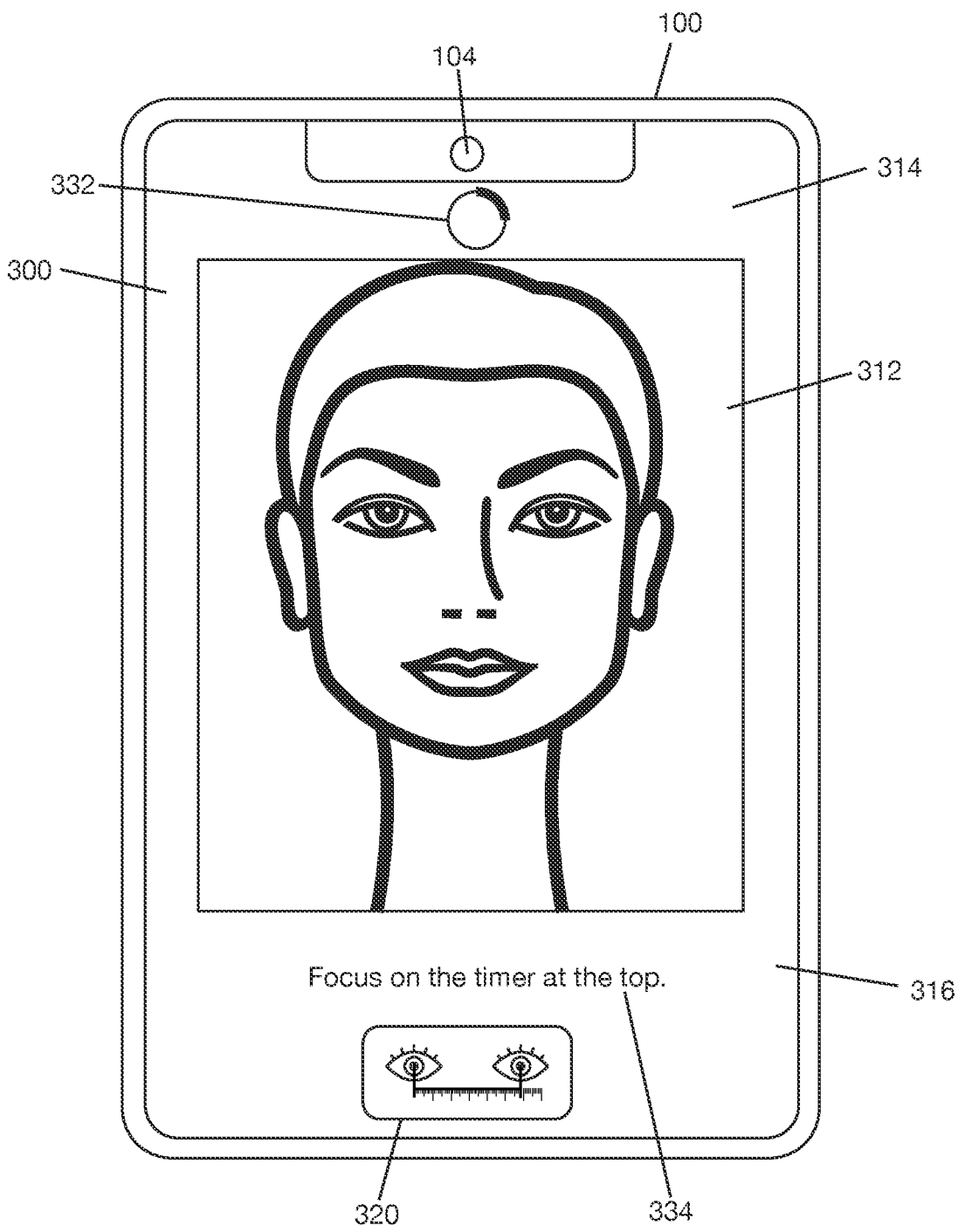
FIGS. 3D and 3E are front views of the electronic device of FIG. 1 showing different states of a processing screen of an app UI.

At 220, the processor may present a gaze focus point on the pupil detection screen of the app UI. The user is expected to focus on the gaze focus point while the FF camera captures images of the frontal portion of the head of the user. The gaze focus point can be any UI element, such as a textual element or a graphical element. Moreover, the UI element may be animated or have features to draw the attention of the user. In some cases, an image of the user shown in a capture window of the app UI may serve as a gaze focus point. For illustrative purposes, FIG. 3D shows an example gaze focus point 332 in top bar 314. Gaze focus point 332 is illustrated as a timer. However, as previously mentioned, any suitable UI element that can provide a focus point may be used as the gaze focus point (e.g., a simple text such as "Look here" or an animation that draws the attention of the user). A cue, such as cue 334, may be displayed in bottom bar 316 to direct the user's gaze to gaze focus point 332.

Figure 3E:
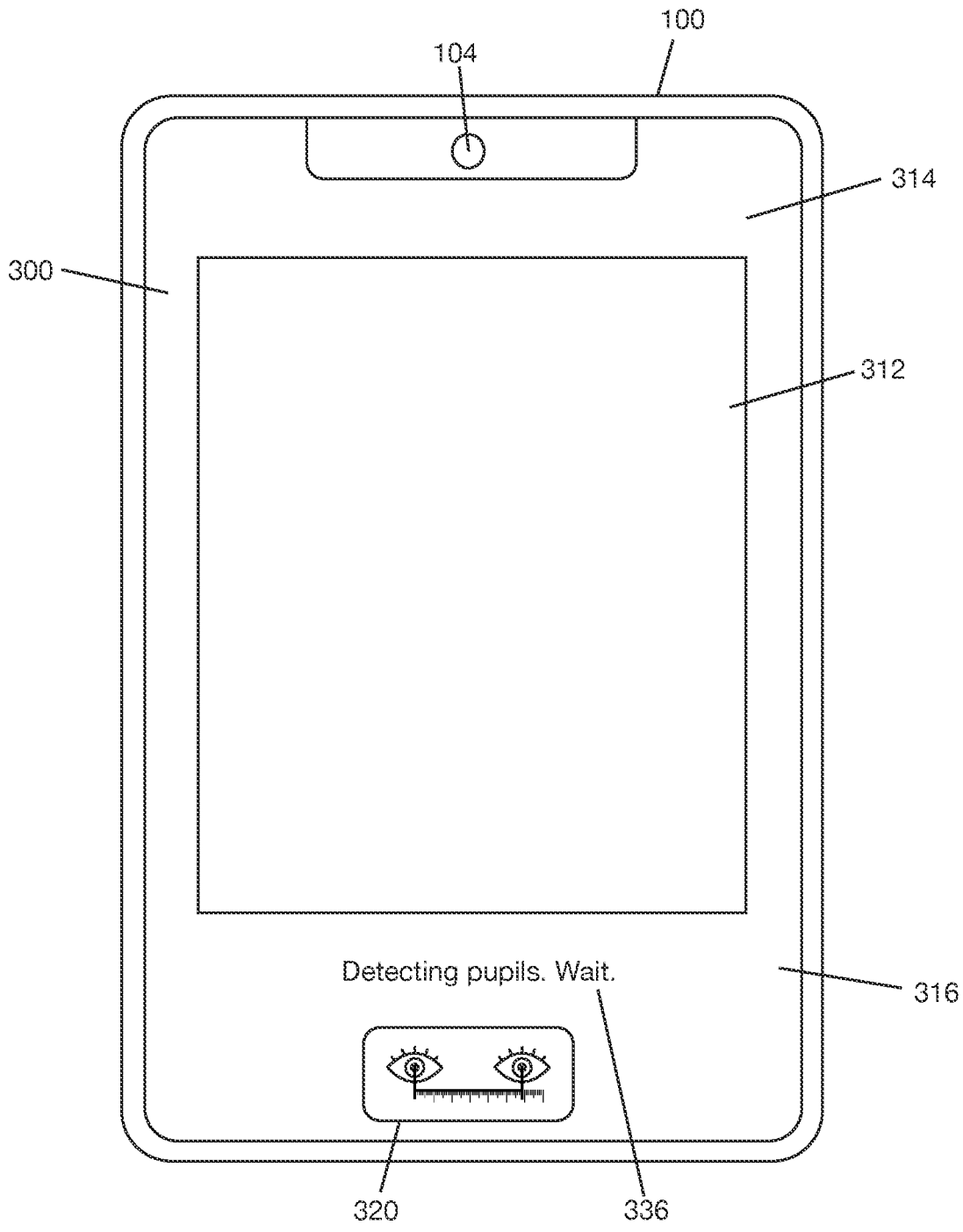

Returning to FIG. 2, at 224, the processor causes the FF camera to capture one or more image frames (or, simply, images) with the FF flash turned on—these FF camera image frames may be referred to as flash-on (FON) images. Turning the flash on is equivalent to illuminating the frontal portion of the head of the user that is captured by the FF camera. Act 224 may be performed with the user gazing at the gaze focus point. After capturing FON image(s) at 224, the processor may turn off the FF camera (and turn off the FF flash) and present a processing screen of the app UI, as indicated at 228. FIG. 3E shows an example of the processing screen of app UI 300 after FF camera 104 has been turned off. In this case, the gaze focus point has been removed because it is no longer needed. Capture window 312 is blank since FF camera 104 has been turned off. A message 336 may be displayed in bottom border 316 to indicate that the app is processing the captured images.

Figure 4:
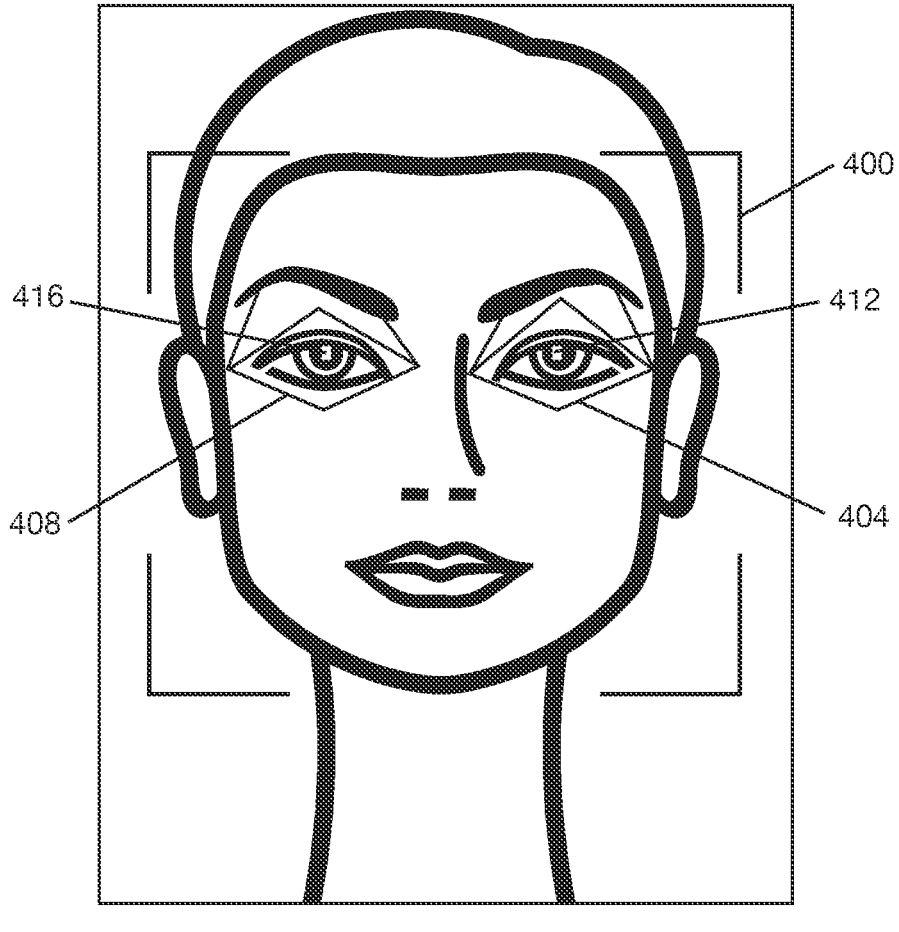
FIG. 4 is a schematic of face regions and eye regions on an image captured by a front facing camera.

Returning to FIG. 2, at 232, the processor selects at least one of the FON images and detects screen reflections on each eye region in the selected FON image (it is not necessary that screen reflections on the left eye and right eye regions are detected from the same FON image, although it may be convenient to do so). Referring to FIG. 4, in one implementation, detecting screen reflections may include detecting a face region 400 from the selected FON image using, for example, a face recognition library such as DLIB. A region of interest (ROI) 404 including the left eye and a ROI 408 including the right eye are detected from face region 400 using a face recognition library. Then, left screen reflection 412 in ROI 404 and right screen reflection 416 in ROI 408 are detected. In one implementation, screen reflections 412, 416 are detected using a convolution based approach.

Figure 5A:
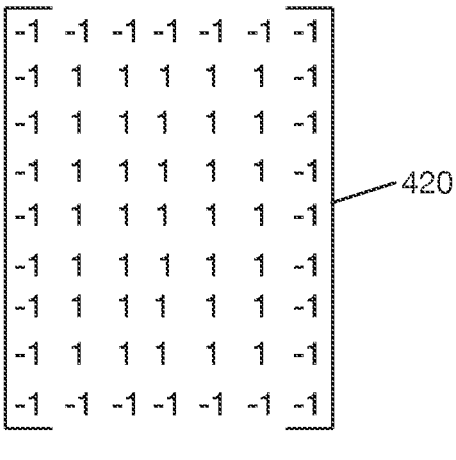
FIG. 5A is an example of a convolution kernel to detect a screen reflection.
Figure 5B:
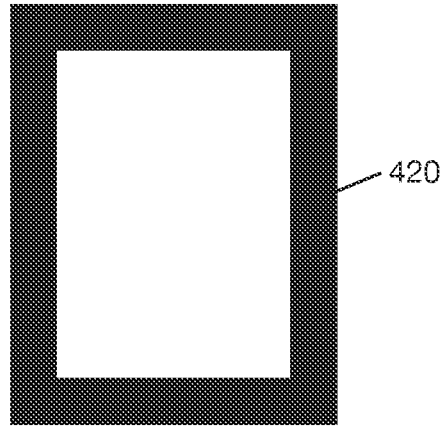
FIG. 5B is an image representation of the convolution kernel of FIG. 5A.

In one example of the convolution based approach, a convolution kernel (or filter) to detect a screen reflection (hereafter referred to as screen reflection kernel) is constructed. In one implementation, the screen reflection kernel is a matrix that favors a bright area that has a screen reflection shape and is surrounded by dark pixels. The screen reflection shape is determined by the shape of the display screen (or known light source) that is reflected onto the eye. In one non-limiting example, the screen reflection shape is rectangular. FIG. 5A shows an example of a screen reflection kernel 420. However, this example is not intended to be limiting since different weights could be used in the matrix than shown in FIG. 5A, and the size of the matrix could be different than what is shown in FIG. 5A. The inner region of the matrix, i.e., the region represented with 1s, will typically have a size that is slightly smaller than the size of the screen reflection to be detected. FIG. 5B shows an image representation of the screen reflection kernel 420, with 1 replaced white a white color and −1 replaced with a black color. The screen reflection kernel (e.g., kernel 420 in FIG. 5A) is convolved with ROI 404 (in FIG. 4) to detect a bright area having a screen reflection shape (e.g., rectangular shape), which corresponds to at least a portion of left screen reflection 412. Similarly, the screen reflection kernel (e.g., kernel 420 in FIG. 5A) is convolved with ROI 408 (in FIG.

4) to detect a bright area having a screen reflection shape (e.g., rectangular shape), which corresponds to at least a portion of right screen reflection 416. Each window of the convolution operation can be normalized by the pixels within the window—this will ensure that windows that have a larger discrepancy between the bright inside areas and dark outer region end up with a higher response after convolution. The neighborhood of the bright areas corresponding to the screen reflections found by the convolution process may be searched to determine the bounds of the detected screen reflections.

Figure 6A:
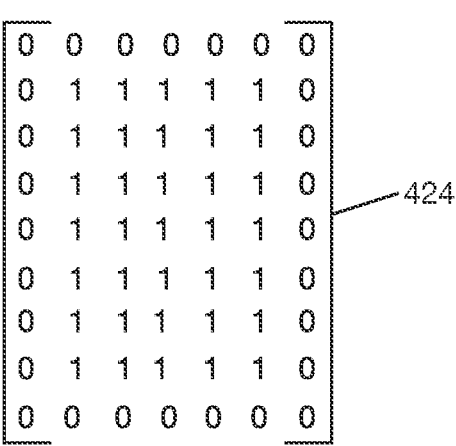
FIGS. 6A-6D are examples of convolution kernels to detect a screen reflection.
Figure 6B:
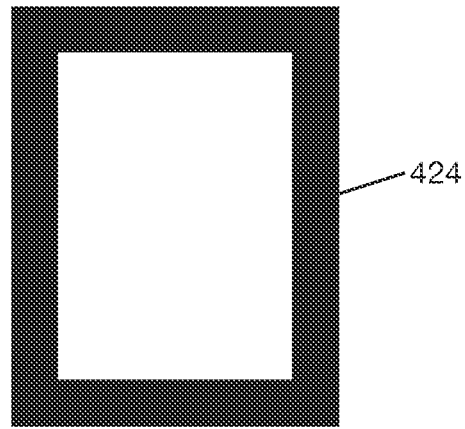
Figure 6C:
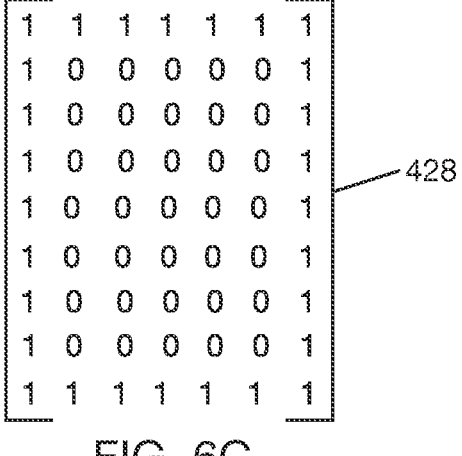
Figure 6D:
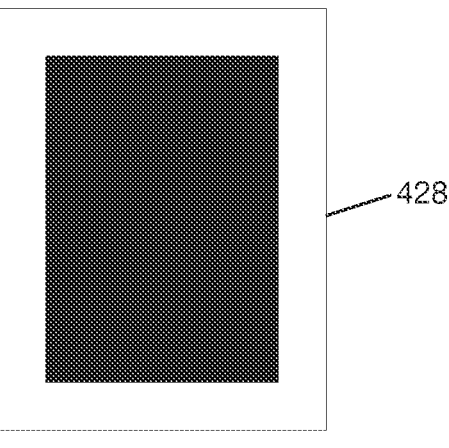

In another convolution approach, two screen reflection kernels are constructed—a first kernel to find the bright area corresponding to a screen reflection and a second kernel to find the dark border around the screen reflection. The first kernel is similar to the screen reflection kernel (e.g., kernel 420 in FIG. 5A) described above, which favors a bright area that has a screen reflection shape and is surrounded by dark pixels, except that the outer region of the first kernel would be 0s, not −1s as in the kernel described above, so that the convolution response does not consider the outside region being dark. FIG. 6A shows a matrix representation of an example first kernel 424. FIG. 6B shows an image representation of first kernel 424, with 1 replaced a white color and 0 replaced with a black color. The second kernel favors dark pixels that surround a bright area having a screen reflection shape. FIG. 6C shows a matrix representation of an example second kernel 428. FIG. 6B shows an image representation of second kernel 428, with 1 replaced with a white color and 0 replaced with a black color. The example kernels shown in FIGS. 6A-6D detect a screen reflection having a rectangular shape. However, kernels that detect screen reflections with other shapes could be similarly constructed. To detect the left screen reflection, each of the first and second kernels (e.g., kernel 424 in FIG. 6A and kernel 428 in FIG. 6B) is convolved with left ROI 404 (in FIG. 4). The result of the convolution with the second kernel is divided by the result of the convolution with the first kernel to obtain a final output image that includes a detected left screen reflection. Similarly, to detect the right screen reflection, each of the first and second kernels is convolved with right ROI 408 (in FIG. 4), and the result of the convolution with the second kernel is divided by the result of the convolution with the first kernel to obtain a final output image that includes a detected right screen reflection. This approach avoids the normalization procedure in the previous convolution approach and speeds up detection of the screen reflections.

If there are multiple reflections from extra light sources (i.e., light sources other than the known light source included in the PED) on any of the eye ROIs (e.g., 404 or 408 in FIG. 4), the screen reflections detected by the convolution processes may not be the ones that correspond to the screen reflections inside the pupils. Therefore, it is useful to check if there may be multiple reflections on the eye ROIs that could interfere with pupillary position detection. Returning to FIG. 2, at 236, the processor determines if a lighting condition of the frontal portion of the head of the user when the selected FON image was captured indicates a bright environment—a bright environment would be indicated if the user was facing one or more light sources other than the known light source (e.g., a window or artificial light or bright reflection off a wall or surface in front of the user) during capture of the FON image. To make this determination, all reflections inside each of eye ROI 404 (in FIG. 4) and eye ROI 408 (in FIG. 4) are detected. In one implementation, all reflections, R, inside each eye ROI are detected using an adaptive threshold, T, that is calculated based on the screen reflection average intensity, Ir (this could be the average intensity of the screen reflection found by the convolution process described above). A reflection $r_i \in R$ is considered as an indication of a bright environment if $\text{dist}(r_i, (c_x, c_y)) < D$ and $\text{area}(r_i) < A$, where dist is the Euclidean distance, area is the area function, and $(c_x, c_y)$ is the detected screen reflection. If one or more reflections meet the above conditions, the lighting condition of the frontal portion of the head of the user when the selected FON image was captured indicates a bright environment.

Figure 7B:
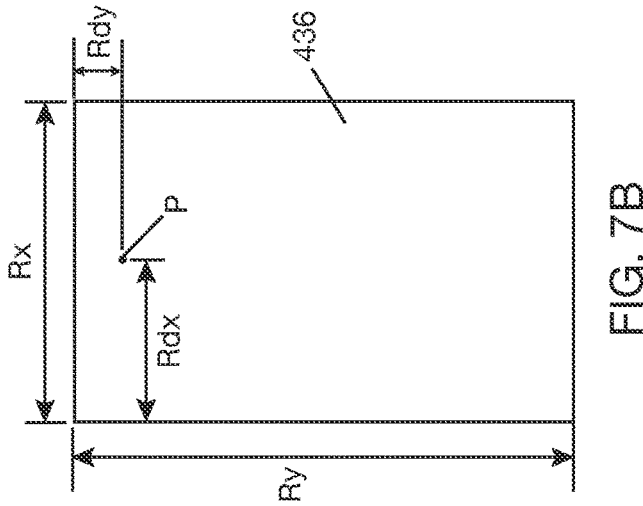
FIGS. 7A and 7B illustrate a proportional relationship between a display screen and a screen reflection.
Figure 7A:
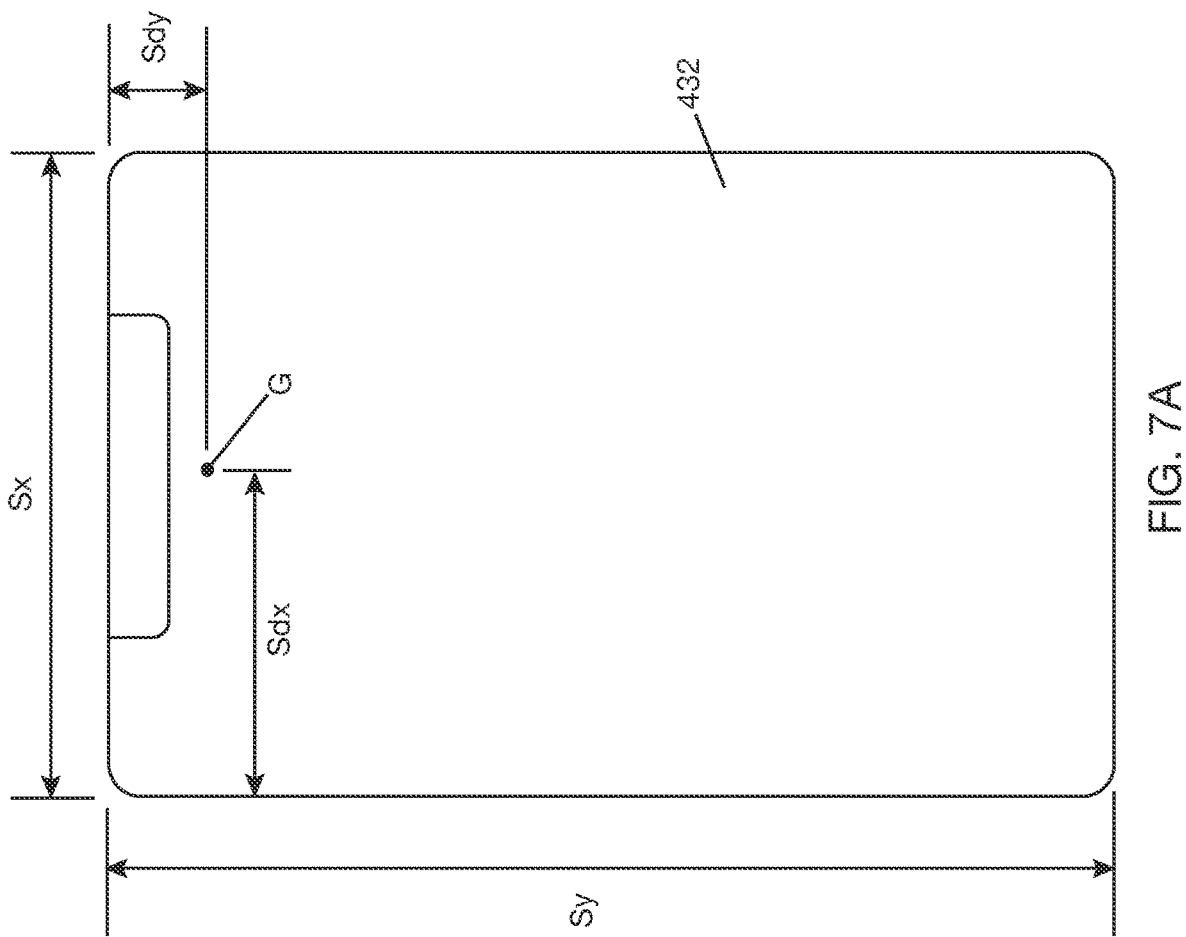

If the processor concludes that the selected FON image was captured in a bright environment, then at 240, the processor discards the FON images captured at 224. The processor may inform the user that the pupil detection failed because the user is facing an unknown light source and may prompt the user to face away from any extra light sources. The processor may stop the eyewear sizing operation and return to 200. Once the user has faced away from extra light sources (i.e., light sources other than the known light source included in the PED), the user may attempt to run the eyewear sizing operation again If the processor concludes that the selected FON image was not captured in a bright environment, then at 244, the processor estimates pupillary positions from the screen reflections detected at 232. Depending on the tolerance for error, any point on the detected left screen reflection may be taken as the left pupillary position (or left pupil center) and any point on the detected right screen reflection may be taken as the right pupillary position (or right pupil center). If a more accurate pupillary position is desired, the left pupillary position may be determined by a proportional relationship between the left screen reflection and the display screen, and the right pupillary position may be determined from a proportional relationship between the right screen reflection and the display screen. For example, FIG. 7A shows a display screen 432 having a height Sy and a width Sx. Gaze focus point G is shown on display screen 432 (this would be where the user focuses when the FON image of the user is captured). Gaze focus point G is vertically displaced from the top edge of the display screen 432 by Sdy and horizontally displaced from the left edge of the display screen by Sdx. FIG. 7B shows a screen reflection 436 (which could be a left or right screen reflection) having a height Ry and a width Rx. A pupil center (or pupillary position) P to be determined is vertically displaced from the top edge of the screen reflection by Rdy and horizontally displaced from the left edge of the screen reflection by Rdx. Rdx and Rdy can be determined by Equations (1) and (2) below since Rx, Ry, Sx, Sy, Sdx, and Sdy are known:

$$\frac{Rdx}{Rx} = \frac{Sdx}{Sx} \tag{1}$$

$$\frac{Rdy}{Ry} = \frac{Sdy}{Sy} \tag{2}$$

Figure 8A:
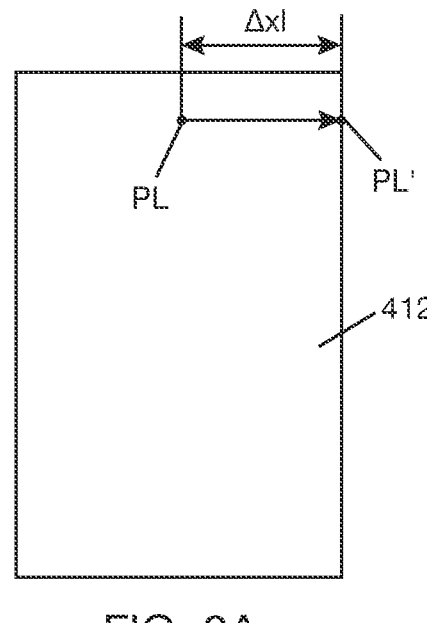
FIG. 8A illustrates lateral shifting of a left pupillary position to compensate for an offset between an optical axis and a visual axis of a left eye.
Figure 8B:
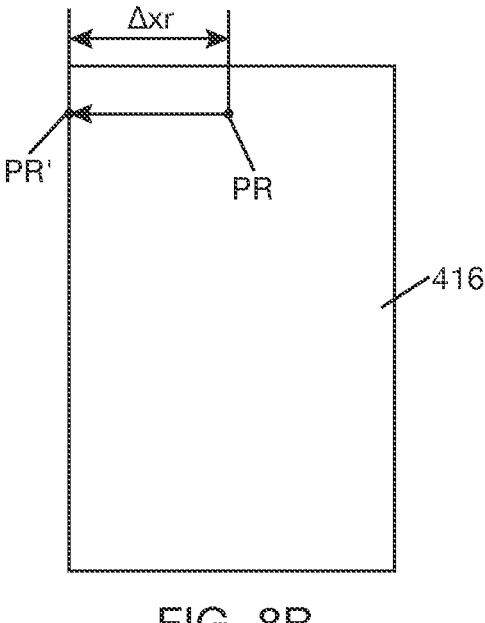
FIG. 8B illustrates lateral shifting of a right pupillary position to compensate for an offset between an optical axis and a visual axis of a right eye.

The left and right pupillary positions obtained by the expressions above may be adjusted to compensate for an offset between the optical axis and the visual axis of the eye. In one example, this includes applying a right offset (right horizontal shift) to the left pupillary position and a left offset (left horizontal shift) to the right pupillary position. In one non-limiting example, a right offset approximately equal to a horizontal displacement of the baseline left pupillary position from the right edge of the left screen reflection offers a suitable compensation for the offset between the optical axis and the visual of the left eye. Similarly, in one non-limiting example, a left offset approximately equal to a horizontal displacement of the baseline right pupillary position from the left edge of the right screen reflection offers a suitable compensation for the offset between the optical axis and the visual axis of the right eye. Baseline left pupillary position and right pupillary position may be determined according to Equations (1) and (2). For illustrative purposes, FIG. 8A shows baseline left pupillary position PL on left screen reflection 412. The horizontal displacement of baseline pupillary position PL from the right edge of screen reflection 412 is represented by $\Delta xl$. If the coordinate of baseline pupillary position PL is (x1, y1), a left pupillary position PL' that compensates for the offset between the optical axis and the visual axis of the eye may be (x1+$\Delta xl$, y), according to one example. However, a different right shift may be applied to PL than shown in FIG. 8B (e.g., one that is less than $\Delta xl$ or greater than $\Delta xl$). FIG. 8B illustrates left shifting of baseline right pupillary position PR on right screen reflection 416 to PR' by an offset $\Delta xr$. If the coordinate of baseline pupillary position PR is (x2, y2), a right pupillary position PR' that compensates for the offset between the optical axis and the visual axis of the eye may be (x2−$\Delta xr$, y2). As described above for the left pupillary position, a different left shift may be applied to PR than shown in FIG. 8B (e.g., one that is less than $\Delta xr$ or greater than $\Delta xr$).

Figure 9B:
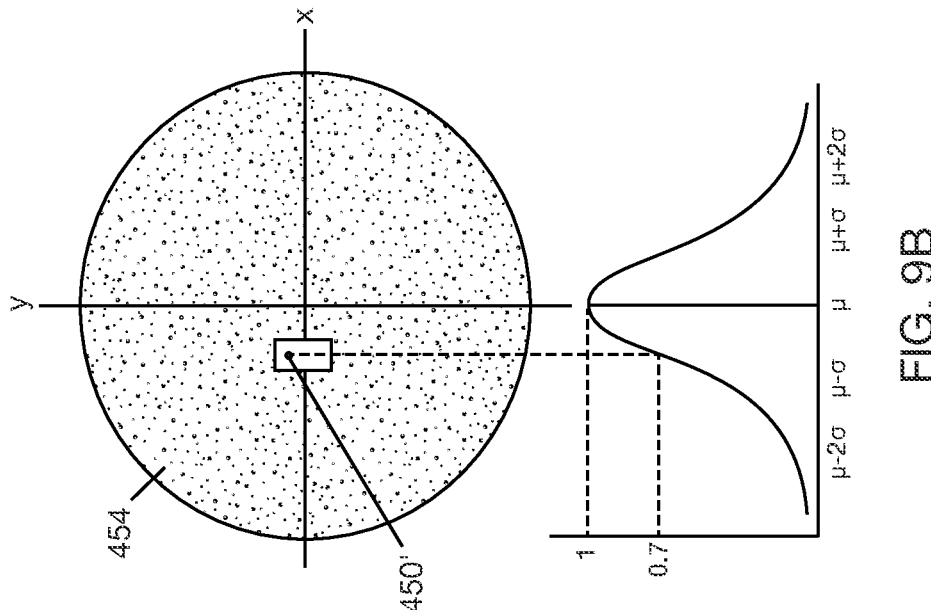
FIG. 9B is a schematic showing offset between an iris center of an eye and a detected pupillary position on the eye.
Figure 9A:
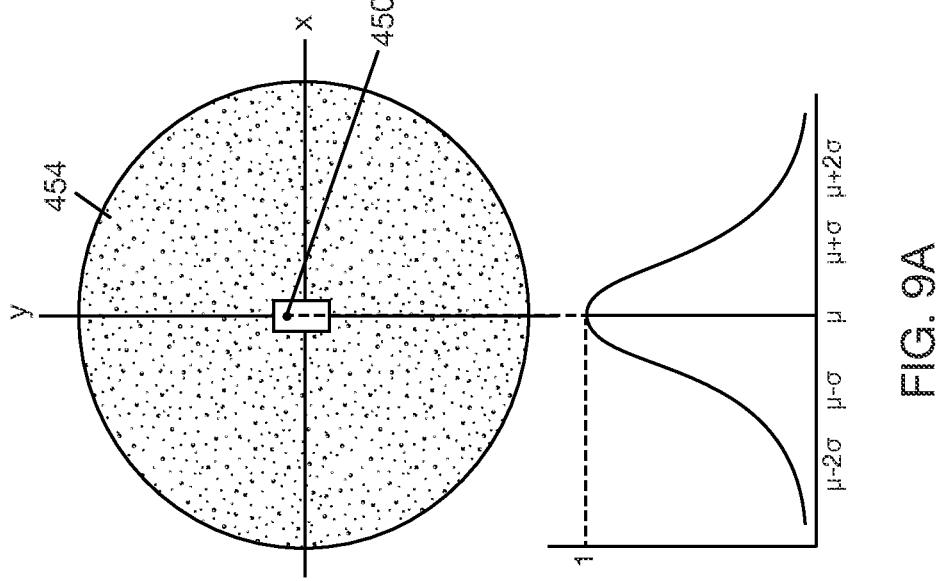
FIG. 9A is a schematic showing alignment of an iris center of an eye with a detected pupillary position on the eye on the eye.

Returning to FIG. 2, at 248, the processor may determine a confidence of the screen reflection detection and resulting estimated pupillary positions. In one example, determining the confidence of the screen reflection detection includes detecting a left iris and a right iris from the selected FON image (or selected FON images). The left iris and right iris may be found by a convolution process using an iris kernel having a generally circular shape that approximates the shape of an iris. The iris is surrounded by the sclera. Thus, the convolution process may detect a non-white area that is surrounded by white pixels. Next, the center of each iris is determined. For each eye, the confidence is calculated as the Gaussian weighted distance of the detected pupillary position from the iris center for the eye. The highest confidence value, 1, occurs when both the iris center and the pupillary position for the eye are aligned. FIG. 9A illustrates a case where a detected pupillary position 450 is aligned with the center of iris 454. In this case, the confidence level is 1. FIG. 9B illustrates a case where detected pupillary position 450' is not aligned with the center of iris 454. The farther away the pupillary position is from the iris center, the lower the confidence of the screen reflection detection. In FIGS. 9A and 9B, the Gaussian weighted distance is calculated horizontally (along x axis). However, the Gaussian weighted distance could be calculated both horizontally (along x axis) and vertically (along y axis) for more accurate measures. In some cases, the Gaussian weighted distances calculated horizontally and vertically could be multiplied with each other to obtain a final confidence value. The pupillary position determined for each eye at 244 will have an associated confidence measure (or a set of associated confidence measures if the Gaussian weighted distance is calculated in the horizontal and vertical directions and the horizontal and vertical Gaussian weighted distances are not combined). The detected pupillary position compared to the iris center in the confidence measure calculations can be the baseline pupillary position or the pupillary position that has been adjusted to compensate for an offset between the optical axis and visual axis of the eye, as previously described.

Returning to FIG. 2, the processor may calculate IPD from the determined pupillary positions. IPD is simply the distance between the left pupillary position and the right pupillary position. The processor may also calculate LPD and RPD—given that the gaze point of the user is known, the simulated pupils can be rotated to estimate a gaze towards infinity, after which the nose bridge center and the two pupillary measurements can be used to calculate LPD and RPD individually. The pupil detection data (e.g., pupillary positions, confidence level of the screen reflection detection, and any calculated IPD, LPD, and RPD) may be stored in memory of the electronic device (e.g., memory 116 in FIG. 1) and/or transmitted to a remote location/server for eyewear or WHUD sizing or for other operations that require information about pupillary positions on a head of a subject.

The above description of illustrated embodiments and implementations, including what is described in the Abstract of the disclosure, is not intended to be exhaustive or to limit the embodiments and implementations to the precise forms disclosed. Although specific embodiments and implementations and examples are described herein for illustrative purposes, various equivalent modifications can be made without departing from the spirit and scope of the disclosure, as will be recognized by those skilled in the relevant art.

What is claimed is:

1. A computer-implemented method of detecting pupillary positions on a head of a subject, the method comprising:
    while a camera and a display screen of an electronic device are positioned in front of the head of the subject, causing the camera to capture image data representative of a frontal portion of the head of the subject;
    detecting a face of the subject from the image data;
    identifying up to two eyes from the detected face;
    detecting a reflection having a shape corresponding to a shape of the display screen on each identified eye; and
    estimating a pupillary position of each identified eye based on a position of the detected reflection of the display screen on the identified eye.

2. The method of claim 1, wherein detecting the reflection of the display screen on each identified eye comprises convolving a region of the detected face including the identified eye with a convolution kernel that is constructed to identify a bright area that has a screen reflection shape and is surrounded by relatively darker pixels.

3. The method of claim 1, wherein detecting the reflection of the display screen on each identified eye comprises convolving a region of the detected face including the identified eye with a first convolution kernel and a second convolution kernel, wherein the first convolution kernel is constructed to identify a bright area having a screen reflection shape and that is surrounded by relatively darker pixels, and wherein the second convolution kernel is constructed to identify dark pixels that surround a relatively brighter area having a screen reflection shape.

4. The method of claim 1, further comprising presenting a gaze focus point on the display screen prior to causing the camera to capture the image data.

5. The method of claim 4, further comprising directing a gaze of the subject to the gaze focus point prior to causing the camera to capture the image data.

6. The method of claim 4, wherein estimating the pupillary position of each identified eye comprises determining a point on the respective detected screen reflection corresponding to the gaze focus point on the display screen.

7. The method of claim 6, wherein estimating the pupillary position of each identified eye further comprises applying a lateral shift to the determined point on the respective detected screen reflection to compensate for an offset between an optical axis and a visual axis of the identified eye.

8. The method of claim 1, further comprising causing the display screen to illuminate the frontal portion of the head of the subject contemporaneously with causing the camera to capture the image data.

9. The method of claim 8, further comprising determining whether a lighting condition of the frontal portion of the head of the subject indicates a bright environment during at least a portion of causing the camera to capture the image data.

10. The method of claim 9, wherein determining whether the lighting condition of the frontal portion of the head of the subject indicates a bright environment comprises:

determining for at least one identified eye whether there are extra light source reflections on the at least one identified eye and comparing an average intensity of each of the extra light source reflections to an average intensity of the detected light source reflection on the at least one identified eye; and wherein the lighting condition of the frontal portion of the head of the subject indicates a bright environment if there is at least one extra light source reflection on the at least one identified eye with an average intensity that substantially matches the average intensity of the detected light source reflection on the at least one identified eye.

11. The method of claim 10, further comprising, if it is determined that the lighting condition of the frontal portion of the head of the subject indicates a bright environment, redoing causing the camera to capture image data representative of the frontal portion of the head of the subject with a different lighting condition.

12. The method of claim 11, further comprising prompting the subject to face away from extra light sources to provide the different lighting condition.

13. The method of claim 1, further comprising determining a confidence of the estimate of the pupillary position of each identified eye based on a degree of displacement of the pupillary position of the identified eye from a center position of an iris on the identified eye.

14. The method of claim 1, further comprising determining at least one of an interpupillary distance, a left pupillary distance, and a right pupillary distance from the estimated pupillary positions.

15. An electronic device for detecting pupillary positions on a head of a subject, the electronic device comprising:

a front facing camera;

a display screen;

at least one processor communicatively coupled to the front facing camera and the display screen; and memory storing a set of instructions that as a result of execution by the at least one processor causes the electronic device to:

while the front facing camera and the display screen are positioned in front of the head of the subject, cause the front facing camera to capture image data representative of a frontal portion of the head of the subject;

detect a face of the subject from the image data;

identify up to two eyes from the detected face;

detect a reflection having a shape corresponding to a shape of the display screen on each identified eye; and estimate a pupillary position of each identified eye based on a position of the detected light source reflection on the identified eye.

16. The electronic device of claim 15, wherein the electronic device is to detect the reflection of the display screen on each identified eye by at least one of:

convolving a region of the detected face including the identified eye with a convolution kernel that is constructed to identify a bright area that has a screen reflection shape and is surrounded by relatively darker pixels; or convolving a region of the detected face including the identified eye with a first convolution kernel and a second convolution kernel, wherein the first convolution kernel is constructed to identify a bright area having a screen reflection shape and that is surrounded by relatively darker pixels, and wherein the second convolution kernel is constructed to identify dark pixels that surround a relatively brighter area having a screen reflection shape.

17. The electronic device of claim 15, wherein execution of the set of instructions by the at least one processor cause the electronic device to present a gaze focus point on the display screen prior to causing the front facing camera to capture the image data.

18. The electronic device of claim 17, wherein execution of the set of instructions by the at least one processor cause the electronic device to direct a gaze of the subject to the gaze focus point prior to causing the front facing camera to capture the image data.

19. The electronic device of claim 17, wherein execution of the set of instructions by the at least one processor cause the electronic device to estimate the pupillary position of each identified eye by determining a point on the respective detected screen reflection corresponding to the gaze focus point on the display screen.

* * * * *